United States Patent [19]

Nielsen

[11] 4,140,866
[45] Feb. 20, 1979

[54] PREPARATION OF SULFATE FREE GLYCOLIC ACID ESTER

[75] Inventor: Donald R. Nielsen, Corpus Christi, Tex.

[73] Assignee: PPG Industries, Inc., Pittsburgh, Pa.

[21] Appl. No.: 891,964

[22] Filed: Mar. 30, 1978

[51] Int. Cl.² ............... C07C 31/20; C07C 67/00; C07C 67/48
[52] U.S. Cl. ............................... 568/864; 560/189
[58] Field of Search ..................... 560/189; 568/864

[56] References Cited

U.S. PATENT DOCUMENTS

| | | | |
|---|---|---|---|
| 2,211,625 | 8/1940 | Loder | 560/189 |
| 2,285,448 | 6/1942 | Loder | 568/864 |
| 2,315,168 | 3/1943 | Urguhart | 560/189 |
| 2,350,964 | 6/1944 | Loder et al. | 560/189 |
| 2,443,482 | 6/1948 | Shattuck | 260/535 |
| 2,568,619 | 9/1951 | Gregory | 560/189 |
| 4,087,470 | 5/1978 | Suzuki | 568/864 |

*Primary Examiner*—Joseph E. Evans
*Attorney, Agent, or Firm*—Edward J. Whitfield

[57] ABSTRACT

Sulfate is removed from glycolic acid, prepared by the sulfuric acid catalyzed carbonylation of formaldehyde and intended for use as an intermediate in the production of ethylene glycol by catalytic hydrogenation by treating the glycolic acid with alkali metal hydroxide or carbonate, and esterifying the glycolic acid; the alkali metal sulfate being substantially completely precipitated in and separated from the esterification product.

12 Claims, 1 Drawing Figure

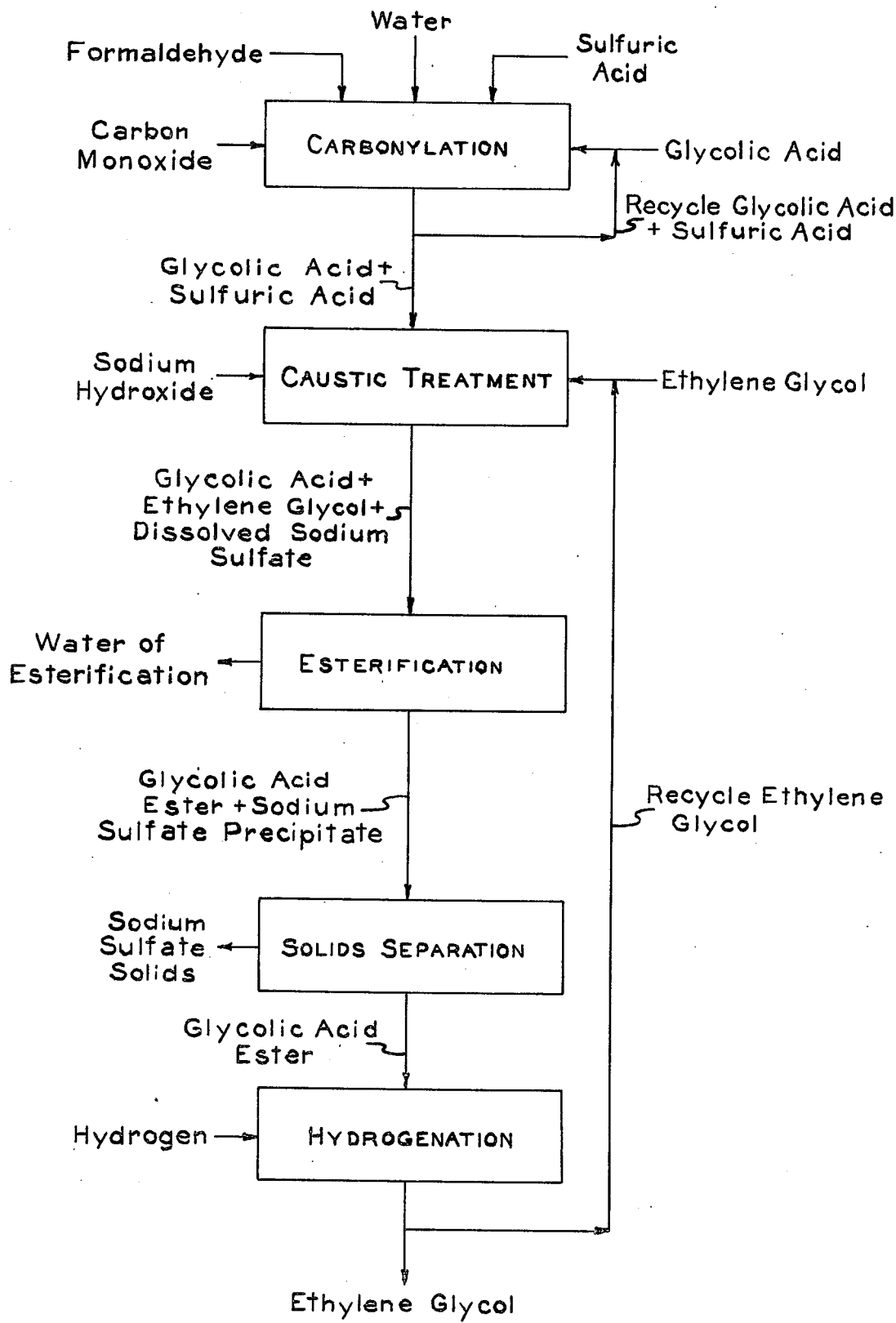

PREPARATION OF SULFATE FREE GLYCOLIC ACID ESTER

BACKGROUND OF THE INVENTION

Ethylene glycol may be prepared by the liquid phase hydrogenation of glycolic acid or esterified glycolic acid in the presence of a suitable hydrogenation catalyst as described, for example, in U.S. Pat. Nos. 2,285,448; 2,607,805; and British Pat. No. 575,380. The glycolic acid is typically prepared by the sulfuric acid catalyzed carbonylation of formaldehyde as described, for example, in U.S. Pat. Nos. 2,152,852 and 2,443,482.

The crude glycolic acid obtained by the sulfuric acid catalyzed carbonylation of formaldehyde typically contains about 1.0 to 3.0 mole percent of sulfuric acid based on the moles of glycolic acid produced. It has been found that catalytic hydrogenation of glycolic acid containing sulfate in amounts typically present from the sulfuric acid catalyzed carbonylation of formaldehyde produces considerably lower yields of ethylene glycol compared with substantially sulfate-free glycolic acid. For example, when a substantially sulfate-free (less than about 0.05 weight percent sulfate) 20 percent aqueous glycolic acid solution was hydrogenated over a reduced cobalt carbonate catalyst at a temperature of 228° C., and pressure of between 3600 to 4100 psig, a 94 percent yield of ethylene glycol was obtained. Under the same conditions using glycolic acid containing 1.9 mole percent sulfate, an ethylene glycol yield of only 74 percent was obtained.

Heretofore, sulfate has typically been removed from glycolic acid prepared by the sulfuric acid catalyzed carbonylation of formaldehyde by neutralization with calcium carbonate or calcium hydroxide to form insoluble calcium sulfate. Calcium sulfate, however, is a very finely divided material, is not readily settleable, and is not readily removed from the relatively viscous glycolic acid by, for example, filtration without using a filter aid such as diatomaceous earth or the like which adds to the sludge disposal problem.

SUMMARY OF THE INVENTION

Sulfate is removed from glycolic acid, prepared by the sulfuric acid catalyzed carbonylation of formaldehyde and intended for use as an intermediate in the production of ethylene glycol, by treating the sulfate-containing glycolic acid with an alkali metal hydroxide or carbonate and esterifying the glycolic acid preferably in the presence of ethylene glycol thereby producing a precipitate of alkali metal sulfate in the esterification product and separating the alkali metal sulfate from the esterification product.

DESCRIPTION OF THE DRAWING

The drawing is a simplified flow sheet of a preferred embodiment of the process of the invention.

DESCRIPTION OF THE INVENTION

In accordance with a preferred embodiment of the invention, crude glycolic acid prepared by the sulfuric acid catalyzed carbonylation of formaldehyde is mixed with ethylene glycol and treated with sufficient sodium hydroxide to convert the sulfuric acid in the glycolic acid to sodium sulfate which is soluble in the glycol/ethylene glycol mixture. The mixture is heated to esterification temperature with removal of evolved water; and as esterification of the glycolic acid proceeds, the heretofore soluble sodium sulfate precipitates as a rapidly settling crystalline material which may be readily removed from the esterification product.

It has been found that sodium sulfate, though soluble in the glycolic acid/ethylene glycol mixture, is substantially insoluble in the esterified glycolic acid, solubility of the sodium sulfate being a function of the extent of esterification. Consequently, in order to precipitate and remove as much sodium sulfate as possible, the glycolic acid should be esterified as completely as possible. In accordance with the invention, glycolic acid ester containing less than 0.05 percent by weight sulfate and typically less than 0.02 percent by weight sulfate can be routinely obtained.

With reference to the drawing, in a typical practice of the invention, a mixture of formaldehyde, water, glycolic acid, and sulfuric acid is reacted in the liquid phase with carbon monoxide, in known manner, at an elevated temperature and super-atmospheric pressure. Although reactant ratios and reaction conditions may vary over a wide range, satisfactory results are typically obtainable at a molar ratio of glycolic acid:water:formaldehyde in the range of from about 1:1:1 to about 2:1:1 using from about 0.1 percent to about 3.0 percent by weight, usually from about 0.3 percent to 2.0 percent by weight, sulfuric acid based on the combined weight of liquid reactants. The reaction is typically conducted at a temperature from about 180° C. to about 220° C. at a carbon monoxide pressure of from about 2,000 to 10,000 psig, preferably from about 3,000 to 4,000 psig for a time sufficient to effect the desired degree of conversion, typically from about one minute to about 30 minutes.

A portion of the crude glycolic acid product may be recycled to the carbonylation stage and the remainder of the crude glycolic acid is mixed with ethylene glycol in a molar ratio of ethylene glycol to crude glycolic acid of about 0.2:1 to 2:1, preferably about 1:1. Sodium hydroxide is added to the ethylene glycol/glycolic acid mixture in an amount sufficient to convert the sulfuric acid in the glycolic acid to sodium sulfate. Large excesses, i.e., greater than about 5 percent, of sodium hydroxide should be avoided and the sodium hydroxide is preferably used in stoichiometric amount based on the amount of sulfuric acid. The ethylene glycol/glycolic acid mixture containing dissolved sodium sulfate is esterified in known manner at a temperature of from about 150° C. to about 200° C., preferably from 165° C. to 175° C. at atmospheric pressure or sub-atmospheric pressure. Esterification is continued, with removal of evolved water, until the acid number of the esterification product is less than about 1.0 mulliequivalent and preferably less than about 0.2 milliequivalents $H^+$ per gram.

The crystalline sodium sulfate precipitate settles out of the relatively viscous solution in a matter of a few seconds and is readily separated from the esterification product by conventional means, such as, for example, filtration, centrifugation, decantation, or the like. After the precipitated sodium sulfate is removed, the glycolic acid ester is catalytically hydrogenated in known fashion to produce ethylene glycol. Hydrogenation of the glycolic acid ester is typically conducted at a temperature of from about 150° C. to about 220° C., preferably from about 180° C. to 190° C., and at a hydrogen pressure of from about 2,000 psig to about 10,000 psig, preferably from about 3,000 to 5,000 psig in the presence of a suitable hydrogenation catalyst, preferably a cobalt-containing catalyst, for a time sufficient to effect the desired degree of conversion, typically from about 30 minutes to one hour. Depending on the choice of reaction conditions and catalytic activity, substantially complete conversion of the glycolic acid ester to ethylene glycol may be obtained. A portion of the product ethylene glycol may be recycled and mixed with the crude sulfuric acid containing glycolic acid.

Although the invention has been described with reference to a preferred embodiment thereof, it is apparent that variations may be made therein which are fully within the scope thereof. For example, potassium hydroxide, sodium carbonate, or potassium carbonate may be used in place of sodium hydroxide or in admixture therewith and the sulfuric acid contained in the crude glycolic acid may be converted to sodium or potassium sulfate prior to mixing the crude glycolic acid with ethylene glycol.

The invention is further illustrated but is not intended to be limited by the following examples.

EXAMPLE 1

A glycolic acid/sulfuric acid mixture of the type typically obtained from the sulfuric acid catalyzed carbonylation of formaldehyde was prepared by adding 11.29 grams of concentrated sulfuric acid to 380 grams of glycolic acid. To the glycolic acid/sulfuric acid mixture was added 310 grams of ethylene glycol and to the resultant mixture was added 10.97 grams anhydrous sodium hydroxide pellets dissolved in 14.28 grams of water. The resultant solution was clear with no trace of solids and contained about 1.41 weight percent sulfate. A Vigreaux distillation column was fitted to the flask containing the solution and the solution was heated by means of a heating mantle. At about 100° C., a white crystalline solid appeared and upon cooling to 35° C. most of the solid redissolved. The temperature was again raised and 90.5 milliliters of water of esterification were distilled off. When the temperature reached 186° C., the heating mantle was removed and the solid completely settled out in a few seconds. A sample of the supernatant liquid taken at 180° C. contained less than 0.02 weight percent sulfate.

EXAMPLE 2

10.04 grams of anhydrous sodium hydroxide pellets were added to a solution of 380 grams glycolic acid, 11.98 grams of concentrated sulfuric acid, and 310 grams of ethylene glycol. The solution, after stirring overnight at ambient temperature, was clear with no trace of solids. The mixture was heated to 130° C. at which point heating was discontinued and the solids were allowed to settle out. A sample of the supernatant liquid contained about 0.91 weight percent sulfate. Heat was again applied and samples of the supernatant liquid were taken when 31, 52, 71, and 80 milliliters of water of esterification had collected in the receiver. The sulfate contents of these samples were found to be 0.45, 0.18, 0.05, and 0.02 weight percent respectively.

EXAMPLE 3

7.10 grams of anhydrous potassium hydroxide pellets were added to 190 grams of glycolic acid containing 6.08 grams of concentrated sulfuric acid. After standing overnight at room temperature, the solution was clear and contained no trace of solids. 154.4 grams of ethylene glycol were added and the resultant solution remained clear with no trace of solids. The solution was heated and a precipitate was observed at about 130° C. A sample of supernatant liquid at this point contained 1.23 weight percent sulfate. Heating was continued until 39 milliliters of water of esterification had been collected and the temperature had reached 207° C. Heating was discontinued, the precipitate was permitted to settle, and a sample of supernatant liquid at 190° C. contained 0.03 weight percent sulfate. The solution was cooled to room temperature and a sample of supernatant liquid after cooling was found to also contain 0.03 weight percent sulfate.

EXAMPLE 4 (Comparison)

423 grams of an aqueous 71 percent glycolic acid solution was placed in a 1-liter, three-necked flask with a thermowell and a Vigreaux distillation column. The solution was heated until a 98.8 grams of water had distilled off. To the distillation residue was added 2.3 grams of concentrated sulfuric acid followed by 1.91 grams of calcium hydroxide. The mixture was stirred at room temperature for 30 minutes and allowed to stand overnight. The following morning the mixture was completely cloudy. 174 grams of ethylene glycol were added and the mixture was then heated, with stirring, to 115° C. for 40 minutes and allowed to stand. After two weeks of quiescent standing, the mixture remained cloudy, and after 25 days of quiescent standing only about one-third of the mixture had clarified.

Although the invention has been described with specific references and specific details of embodiments thereof, it is to be understood that it is not intended to be so limited since changes and alterations therein may be made by those skilled in the art which are within the full intended scope of this invention as defined by the appended claims.

I claim:

1. A process for preparing substantially sulfate free glycolic acid ester from sulfuric acid containing glycolic acid comprising treating said glycolic acid with alkali metal hydroxide or carbonate to convert sulfuric acid contained therein to soluble alkali metal sulfate, esterifying the so-treated glycolic acid so as to precipitate alkali metal sulfate from the esterified glycolic acid.

2. The process of claim 1 wherein the alkali metal hydroxide or carbonate is selected from sodium hydroxide, potassium hydroxide, sodium carbonate, or potassium carbonate.

3. The process of claim 1 wherein the acid number of the esterified glycolic acid is less than 1.0 milliequivalent $H^+$ per gram.

4. The process of claim 3 wherein the acid number of the esterified glycolic acid is less than 0.2 milliequivalent $H^+$ per gram.

5. The process of claim 1 wherein the glycolic acid is esterified in the presence of ethylene glycol.

6. The process of claim 5 wherein the glycolic acid is mixed with ethylene glycol prior to converting the sulfuric acid to alkali metal sulfate.

7. In a process for preparing ethylene glycol by the liquid phase catalytic hydrogenation of glycolic acid ester prepared by esterifying glycolic acid that had been prepared by the sulfuric acid catalyzed liquid phase carbonylation of formaldehyde, the improvement comprising treating the crude glycolic acid obtained from the sulfuric acid catalyzed carbonylation of formaldehyde with alkali metal hydroxide or carbonate to convert the sulfuric acid contained in the glycolic acid to soluble alkali metal sulfate and esterifying the glycolic acid containing the dissolved alkali metal sulfate so as to precipitate alkali metal sulfate and separating the precipitated alkali metal sulfate from the esterification product prior to subjecting the esterification product to catalytic liquid phase hydrogenation.

8. The process of claim 7 wherein the alkali metal hydroxide or carbonate is selected from sodium hydroxide, potassium hydroxide, sodium carbonate, or potassium carbonate.

9. The process of claim 7 wherein the acid number of the esterified glycolic acid is less than 1.0 milliequivalent $H^+$ per gram.

10. The process of claim 9 wherein the acid number of the esterified glycolic acid is less than 0.2 milliequivalent $H^+$ per gram.

11. The process of claim 7 wherein the glycolic acid is esterified in the presence of ethylene glycol.

12. The process of claim 11 wherein the glycolic acid is mixed with the ethylene glycol prior to converting the sulfuric acid to alkali metal sulfate.

* * * * *